US00PP21394P3

(12) United States Plant Patent
Bourne

(10) Patent No.: US PP21,394 P3
(45) Date of Patent: Oct. 19, 2010

(54) ***DIANTHUS* PLANT NAMED 'WP08 VER03'**

(50) Latin Name: *Dianthus×hybrida*
Varietal Denomination: WP08 VER03

(76) Inventor: Carolyn Grace Bourne, Houndspool, Ashcombe Road, Dawlish, Devon (GB) Ex7 0QP ( * ) Notice: Subject to any disclaimer, the term of this patent is extended or adjusted under 35 U.S.C. 154(b) by 0 days.

(21) Appl. No.: 12/456,950

(22) Filed: Jun. 24, 2009

(65) Prior Publication Data

US 2009/0328263 P1 Dec. 31, 2009

(51) Int. Cl.
*A01H 5/00* (2006.01)

(52) U.S. Cl. ..... Plt./272

(58) Field of Classification Search ..... Plt./272
See application file for complete search history.

*Primary Examiner*—Annette H Para

(57) ABSTRACT

A new cultivar of *Dianthus* plant named 'WP08 VER03' whose flowers are pleasantly perfumed, double and bi-colored lavender-pink with a maroon "eye" and comprised of deeply fimbriated petals. In combination these traits set 'WP08 VER03' apart from all other existing varieties of *Dianthus* known to the inventor.

2 Drawing Sheets

Genus: *Dianthus.*
Species: *×hybrida.*
Denomination: 'WP08 VER03'.

BACKGROUND OF THE INVENTION

This application claims the benefit of priority under 35 U.S.C. 119(f) of the application for a grant of European Community Plant Breeders Rights which was filed for the instant plant variety on Jun. 30, 2008, Application Number 2008/1507.

The present invention relates to a new and distinct cultivar of hardy garden pink or carnation which is grown for use as a flowering plant for pots and containers and for planting in the garden or landscape. The new cultivar is known botanically as *Dianthus×hybrida* and will be referred to hereinafter by the cultivar name 'WP08 VER03'.

'WP08 VER03' is a complex hybrid plant that is the product of a breeding program started by the inventor in 1985. The breeding program is conducted in a cultivated area of Houndspool, Dawlish, Devon, United Kingdom. The inventor selected 'WP08 VER03' in 2003 for its flowers which are double and bi-colored lavender-pink with a maroon "eye". The petals of 'WP08 VER03' are deeply fimbriated and flowers are pleasantly perfumed.

'WP08 VER03' resulted from the open pollination between the inventor's unreleased and unpatented seedling selection *Dianthus* code number WE03 as female parent plant and an unknown seedling as male parent plant.

'WP08 VER03' is distinguishable from the female parent as follows: Whereas 'WP08 VER03' bears double flowers which are colored lavender pink with a maroon eye, the flowers of the female parent are semi-double and are colored white with a dark magenta eye.

The variety of *Dianthus* which is considered by the inventor to most closely resemble 'WP08 VER03' is the inventor's variety, *Dianthus* 'Devon Esther' (U.S. Plant Pat. No. 18,222). 'WP08 VER03' is distinguishable from 'Devon Esther' as follows: The flowers of 'WP08 VER03' are more fully double with greater fimbriation of the petals than the flowers of 'Devon Esther'. The flowers of 'Devon Esther' are darker purple-pink in color than the lavender-pink color of the flowers of 'WP08 VER03'.

Asexual reproduction of the new cultivar was first accomplished by the inventor in 2003 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP08 VER03'. These traits in combination distinguish this cultivar from all other commercial varieties known to the inventor. 'WP08 VER03' has not been tested under all possible conditions and phenotypic differences may be observed with variations in environmental, climatic and cultural conditions, however, without any variance in genotype.

1. *Dianthus* 'WP08 VER03' exhibits a compact habit.
2. *Dianthus* 'WP08 VER03' blooms profusely from April until October.
3. The flowers of *Dianthus* 'WP08 VER03' are double and bi-colored lavender-pink with a maroon "eye".
4. The flowers of 'WP08 VER03' are pleasantly fragrant.
5. The petals of the flowers of 'WP08 VER03' are deeply fimbriated.
6. *Dianthus* 'WP08 VER03' exhibits grey-green foliage.
7. At maturity, the height of the foliage mound of *Dianthus* 'WP08 VER03' is 20 cm to 25 cm; the width is 10 cm to 12 cm.
8. *Dianthus* 'WP08 VER03' is perennial and is hardy to −15° C.

BRIEF DESCRIPTION OF THE DRAWINGS

The accompanying color drawings illustrate the overall appearance of the new *Dianthus* variety 'WP08 VER03' showing colors as true as it is reasonably possible to obtain in colored reproductions of this type. Colors in the drawings may differ from the color values cited in the detailed botanical description, which accurately describe the actual colors of the new variety 'WP08 VER03'.

The drawing labeled as FIG. 1 depicts an entire flowering plant.

Figure 1:
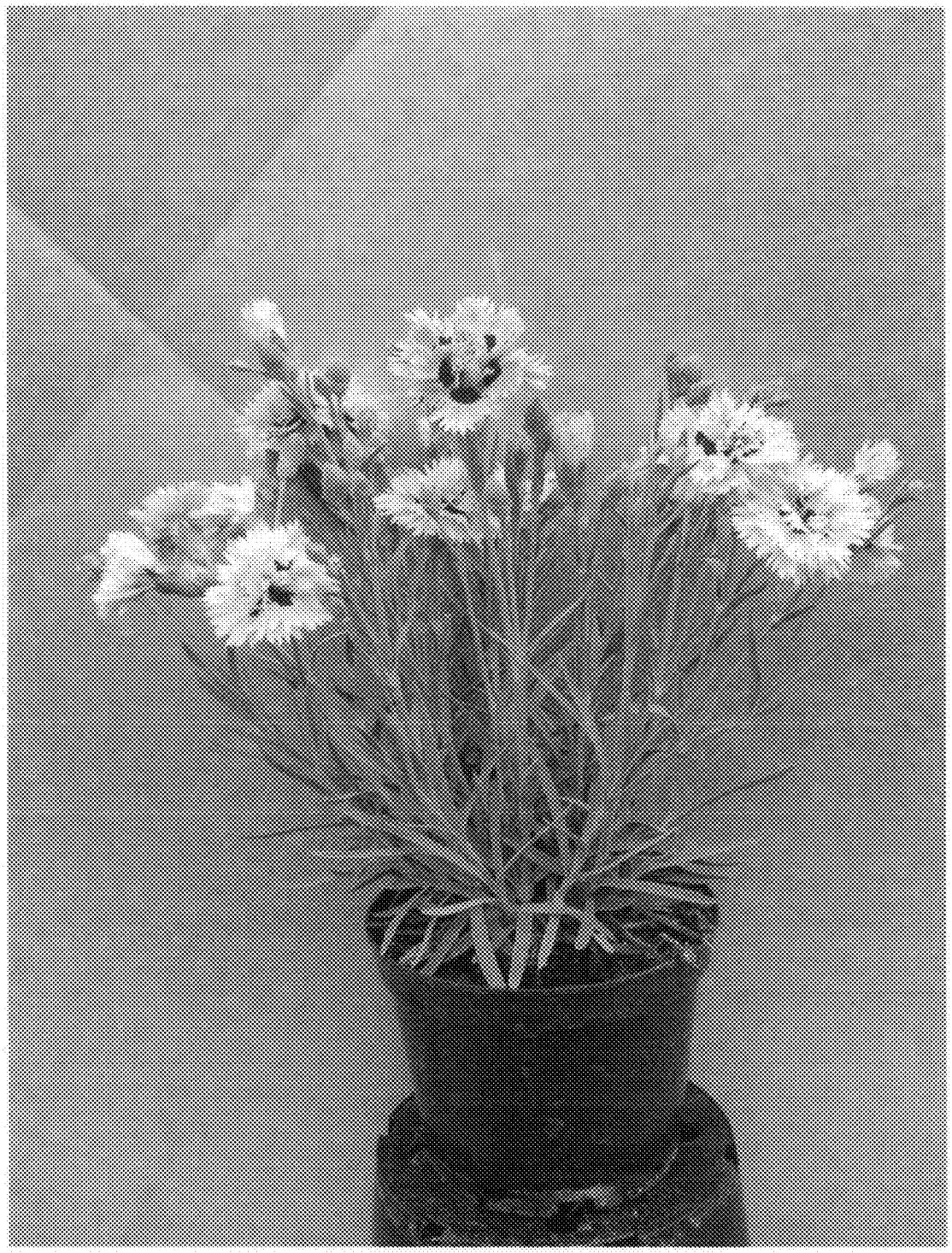
Figure 2:
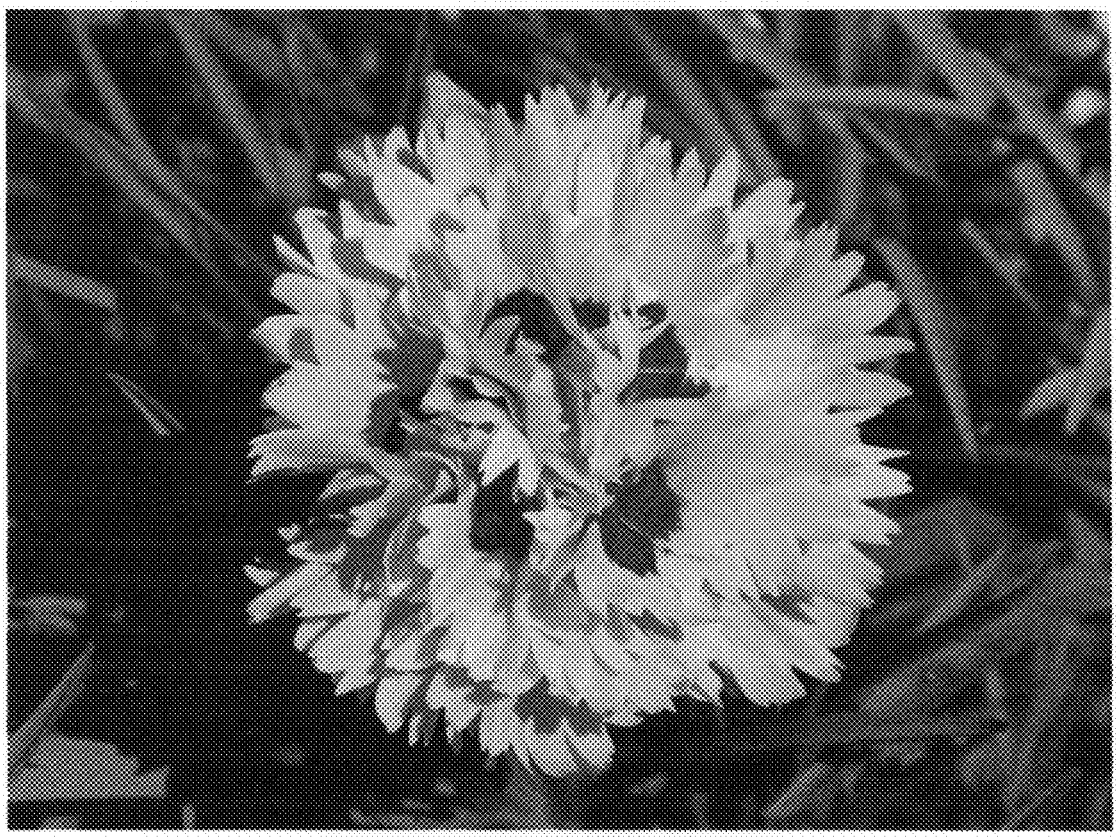

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP08 VER03'. Data was collected in spring from 1.5-liter container plants in spring, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family.*—Caryophyllaceae.
- *Genus.*—*Dianthus.*
- *Species.*—×*allwoodii.*
- *Denomination.*—'WP08 VER03'.

Parentage: A complex *Dianthus* hybrid whose immediate parents are unreleased hybrids from the inventor's breeding program, identified as follows:
- *Male parent.*—Selection Unknown.
- *Female parent.*—Selection WE03.

Plant type: Flowering perennial.

Use of plant: As a flowering plant in containers, window boxes, planters, pots and the garden.

Bloom period: April-October.

Plant habit: A compact mound with many branches and upright stems.

Height of plant: 20 to 25 cm after 9 months.

Width of plant: 10 to 12 cm after 9 months.

Hardiness: To minus 15 Centigrade depending on the environment.

Type: Perennial herb.

Root system: Many fibrous roots.

Propagation method: By vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: A mist propagation unit is required for satisfactory rooting of cuttings.

Crop time: 3 months starting in the Spring and 6 months starting in the Fall.

Plant stem:
- *Shape.*—Cylindrical.
- *Dimensions.*—Height: 7 to 9 cm, diameter: 4 mm.
- *Surface.*—Glabrous and glaucous.
- *Color.*—145B to 145C in the node zone.
- *Branching.*—Numerous shoots from the axils of the lower leaves.
- *Internode length* (*between nodes*).—5 to 7 mm.

Leaf:
- *Type.*—Evergreen.
- *Shape.*—Linear, straight.
- *Division.*—Simple.
- *Apex.*—Acute.
- *Base.*—Decurrent.
- *Venation.*—Not prominent.
- *Margins.*—Entire.
- *Arrangement.*—Opposite and spiraling on stem.
- *Attachment.*—Sheathing.
- *Surface adaxial.*—Glaucous.
- *Surface abaxial.*—Glaucous.
- *Fragrance.*—Absent.
- *Dimensions.*—Length: 45 to 55 mm. Width: 5 mm.
- *Color adaxial surface.*—189A-189B.
- *Color abaxial surface.*—189A-189B.

Inflorescence:
- *Flower stem dimension.*—Length: 15 to 25 cm. Width: 3 to 4 mm. Stem strength: Erect. Color: 122B-122C.
- *Inflorescence.*—Cymose.
- *Type.*—Salviform, symmetrical.
- *Development.*—Singly, in sequence from the uppermost bud.

Buds:
- *Color.*—191C.
- *Dimensions.*—13 cm in length (height) and 10 cm in diameter.
- *Shape.*—Conical with rounded base.

Flowers:
- *Number.*—4 to 6 per stem.
- *Dimensions.*—Length including calyx: 30 to 35 mm. Diameter: 45 to 50 mm.
- *Flower shape.*—Circular.
- *Flower profile.*—Flat to slightly convex.
- *Lastingness.*—10 days at 20° C., on or off the plant.
- *Fragrance.*—Medium to strong pleasant perfume.
- *Flowering period.*—April to October.

Corolla:
- *Shape* (*upper part of corolla*).—Flat to slightly convex.
- *Shape* (*lower part of corolla*).—Flat to slightly concave.
- *Petal arrangement.*—Persistent, double, overlapping.
- *Petal margin.*—Serrate.
- *Indentation.*—Up to 4 mm deep.
- *Petal texture.*—Soft.
- *Flower type.*—Double.
- *Petal number.*—25 with additional 5 to 10 petaloid stamens.
- *Petal dimension.*—Length: 35 to 36 mm. Width: 23 to 24 mm.
- *Color pattern.*—Blade is light pink with a purple band.
- *Color of upper surface.*—Ground color of blade: 75A-75B. Color of band across blade (forms the "eye"): 59A-59B. Color of middle of strap: 145C. Color of base of strap: 145D.

*Color of lower surface.*—Ground color of blade: 75C. Color of band across blade: 75C. Color of middle of strap: 145C. Color of base of strap: 145D.

*Petal shape.*—Obdeltoid.

*Petal surface.*—Slightly hairy in the band across blade, flat to undulating.

Calyx:

*Shape.*—Cylindrical.

*Longitudinal profile.*—Convex.

*Dimensions.*—Length: 17 mm. Diameter: 12 mm.

*Sepals.*—Fused.

*Sepals number.*—5.

*Sepals color.*—Upper surface 143A to 139B, lower surface 145B.

*Anthocyanin.*—Present on the edge of the lobes.

*Splitting.*—Yes.

Epicalyx:

*Bracts number.*—1 pair of 2.

*Shape of outer lobe.*—Acuminate.

*Dimensions.*—Width: 8 to 10 mm. Length: 7 to 8 mm.

*Color.*—Upper surface N138C, lower surface 145B.

*Anthocyanin.*—Absent.

Bracteoles:

*Number.*—1 pair of 2.

*Dimensions.*—Width: 10 to 12 mm. Length: 9 mm.

*Color.*—Upper surface N138C, lower surface 145B.

*Anthocyanin.*—Absent.

Reproductive organs:

*Stamens.*—Number: 5 to 10 (typically 5 are normally developed and 5 are deformed and/or very small). Color of filaments: White. Dimensions: Length: 21 to 23 mm. Diameter: 0.5 mm.

*Anthers.*—Number: 5 to 10. Color: 84C. Dimensions: Length: 3 mm. Diameter: 1 mm. Attachment: Basifixed.

*Pollen.*—Present occasionally. Color: 157A.

*Style.*—Number: 2 to 3. Shoulder: Absent. Color: White.

*Dimensions* (*at maturity, style plus stigma*).—Length: 20 mm. Width: 0.5 mm.

*Stigma.*—Number: 2 to 3 (only one stigma per style). Color: 76A to 77D.

*Ovary.*—Position: Superior. Dimensions: Length: 5 mm. Diameter: 4 mm. Shape: Spindle. Color (upper surface): 145B. Color (lower surface):145C.

*Seed.*—Not observed.

The invention claimed is:

1. A new and distinct cultivar of *Dianthus* plant named 'WP08 VER03' as described and illustrated herein.

* * * * *